(12) United States Patent
Refior et al.

(10) Patent No.: US 6,875,210 B2
(45) Date of Patent: Apr. 5, 2005

(54) ELECTROSURGICAL GENERATOR AND METHOD FOR CROSS-CHECKING MODE FUNCTIONALITY

(75) Inventors: Tim Refior, Parker, CO (US); Jim Pantera, Brighton, CO (US)

(73) Assignee: ConMed Corporation, Utica, NY (US)

( * ) Notice: Subject to any disclaimer, the term of this patent is extended or adjusted under 35 U.S.C. 154(b) by 149 days.

(21) Appl. No.: 10/299,952

(22) Filed: Nov. 19, 2002

(65) Prior Publication Data

US 2004/0097913 A1 May 20, 2004

(51) Int. Cl.$^7$ ............................................. A61B 18/04
(52) U.S. Cl. ....................................................... 606/34
(58) Field of Search .......................... 606/32–35, 37–41

(56) References Cited

U.S. PATENT DOCUMENTS

| | | |
|---|---|---|
| 4,303,073 A | 12/1981 | Archibald |
| 4,416,276 A | 11/1983 | Newton et al. |
| 4,416,277 A | 11/1983 | Newton et al. |
| 4,574,801 A | 3/1986 | Manes |
| 4,651,280 A | 3/1987 | Chang et al. |
| 4,658,819 A | 4/1987 | Harris et al. |
| 4,712,544 A | 12/1987 | Ensslin |
| 4,781,175 A | 11/1988 | McGreevy et al. |
| 4,819,752 A | 4/1989 | Zelin |
| 4,848,335 A | 7/1989 | Manes |
| 4,860,745 A * | 8/1989 | Farin et al. .................. 606/40 |
| 5,087,257 A | 2/1992 | Farin et al. |
| 5,300,068 A | 4/1994 | Rosar et al. |
| 5,318,563 A * | 6/1994 | Malis et al. .................. 606/38 |
| 5,370,645 A * | 12/1994 | Klicek et al. .................. 606/35 |
| 5,372,596 A | 12/1994 | Klicek et al. |
| 5,422,567 A | 6/1995 | Matsunaga |
| 5,423,810 A | 6/1995 | Goble et al. |
| 5,520,633 A | 5/1996 | Costin |
| 5,540,681 A | 7/1996 | Strul et al. |
| 5,573,533 A | 11/1996 | Strul |
| 5,584,830 A | 12/1996 | Ladd et al. |
| 5,599,344 A | 2/1997 | Paterson |
| 5,733,281 A | 3/1998 | Nardella |
| 6,139,546 A | 10/2000 | Koenig et al. |
| 6,165,173 A | 12/2000 | Kamdar et al. |
| 6,210,403 B1 * | 4/2001 | Klicek .......................... 606/34 |
| 6,228,079 B1 | 5/2001 | Koenig |
| 6,231,569 B1 | 5/2001 | Bek et al. |
| 6,261,286 B1 | 7/2001 | Goble et al. |
| 6,264,653 B1 * | 7/2001 | Falwell ......................... 606/41 |
| 6,293,941 B1 | 9/2001 | Strul et al. |
| 6,309,386 B1 | 10/2001 | Bek |
| 6,398,779 B1 | 6/2002 | Buysse et al. |

FOREIGN PATENT DOCUMENTS

| | | |
|---|---|---|
| EP | 0332308 | 9/1989 |
| WO | WO 0236028 | 5/2002 |

OTHER PUBLICATIONS

H. Hölscher et al., *Microcomputers in Safety Technique, An Aid to Orientation for Developer and Manufacturer*, 1986, Chapter 1–1 through 8–9.

International Search Report for the PCT application PCT/US 03/34076 which corresponds to the present U.S. application.

* cited by examiner

*Primary Examiner*—Michael Peffley
(74) *Attorney, Agent, or Firm*—John R. Ley (57) ABSTRACT

The functionality and the mode of operation are evaluated in an electrosurgical generator by determining whether a patterned pulse signal that contributes to the generation of electrosurgical energy is as expected. A number of pulses in the patterned pulse signal is compared to an expected number of pulses, and an error condition is indicated when the two values are not the same or differ by more than a predetermined amount. The expected number of pulses depends on a mode of operation of the electrosurgical generator. The error condition may be used to as a basis to terminate the output power delivery.

49 Claims, 3 Drawing Sheets

ELECTROSURGICAL GENERATOR AND METHOD FOR CROSS-CHECKING MODE FUNCTIONALITY

CROSS REFERENCE TO RELATED APPLICATION

This invention and application is related to an invention for an Electrosurgical Generator and Method for Cross-Checking Output Power, described in U.S. patent application Ser. No. 10/299,988, and to an invention for Electrosurgical Generator and Method with Multiple Semi-Autonomously-Executable Functions, described in U.S. patent application Ser. No. 10/299,953, which are filed concurrently herewith and assigned to the assignee of the present invention. The subject matter of these concurrently filed applications is incorporated herein by this reference.

FIELD OF THE INVENTION

This invention generally relates to electrosurgery. More specifically, the invention relates to a new and improved electrosurgical generator and method that checks the mode of operation of the electrosurgical generator to assure proper functionality of the electrosurgical generator and that the desired electrosurgical clinical effect is delivered during the surgical procedure.

BACKGROUND OF THE INVENTION

Electrosurgery involves applying relatively high voltage, radio frequency (RF) electrical power to tissue of a patient undergoing surgery, for the purpose of cutting the tissue, coagulating or stopping blood or fluid flow from the tissue, or cutting or coagulating the tissue simultaneously. The high voltage, RF electrical power is created by an electrosurgical generator, and the electrical power from the generator is applied to the tissue from an active electrode manipulated by a surgeon during the surgical procedure.

The amount and characteristics of the electrosurgical energy delivered to the patient is determined by the surgeon and depends on the type of procedure, among other things. For example, cutting is achieved by delivering a continuous RF signal ranging up to relatively high power, for example 300 watts. Coagulation is achieved by rapidly switching the RF power on and off in a duty cycle. The coagulation duty cycle has a frequency considerably lower than the RF power delivered. However, during the on-time of each duty cycle, the electrical power is delivered at the RF frequency. The power delivered during coagulation is typically in the neighborhood of approximately 40–80 watts, although power delivery as low as 10 watts or as high as 110 watts may be required. Simultaneous cutting and coagulation, which is also known as a "blend" mode of operation, also involves a duty cycle delivery of RF energy, but the on-time of the duty cycle during blend is greater than the on-time of the duty cycle during coagulation. Power is delivered at the RF frequency because the frequency is high enough to avoid nerve stimulation, thereby allowing the tissue to remain somewhat stationary without contractions caused by the electrical energy.

The electrosurgical generator must also have the capability to deliver a relatively wide range of power. The resistance or impedance of the tissue may change radically from point-to-point during the procedure, thereby increasing the power regulation requirements for the electrosurgical generator. For example, a highly fluid-perfused tissue, such as the liver, may exhibit a resistance or impedance in the neighborhood of 40 ohms. Other tissue, such as the marrow of bone, may have an impedance in the neighborhood of 900 ohms. The fat or adipose content of the tissue will increase its impedance. The variable characteristics of the tissue require the electrosurgical generator to be able to deliver effective amounts of power into all types of these tissues, on virtually an instantaneously changing basis as the surgeon moves through and works with the different types of tissues at the surgical site.

These wide variations in power delivery encountered during electrosurgery impose severe performance constraints on the electrosurgical generator. Almost no other electrical amplifier is subject to such rapid response to such widely varying power delivery requirements. Failing to adequately regulate and control the output power may create unnecessary damage to the tissue or injury to the patient or surgical personnel. In a similar manner, failing to adequately establish the electrical characteristics for cutting, coagulating or performing both procedures simultaneously can also result in unnecessary tissue damage or injury.

Almost all electrosurgical generators involve some form of output power monitoring circuitry, used for the purpose of controlling the output power. The extent of power monitoring for regulation purposes varies depending upon the type of mode selected. For example, the coagulation mode of operation does not generally involve sensing the voltage and current delivered and using those measurements to calculate power for the purpose of regulating the output power. However, in the cut mode of operation, it is typical to sense the output current and power and use those values as feedback to regulate the power delivered.

In addition to power regulation capabilities, most electrosurgical generators have the capability of determining error conditions. The output power of the electrosurgical generator is monitored to ensure that electrosurgical energy of the proper power content and characteristics is delivered. An alarm is generated if an error is detected. The alarm may alert the surgeon to a problem and/or shut down or terminate power delivery from the electrosurgical generator.

Certain types of medical equipment controlled by microprocessors or microcontrollers utilize multiple processors for backup and monitoring purposes. Generally speaking, one of the processors serves as a control processor to primarily control the normal functionality of the equipment. Another one of the processors serves as a monitor processor which functions primarily to check the proper operation of the control processor and the other components of the medical equipment. Using one processor for primary control functionality and another processor for primary monitoring functionality has the advantage of achieving redundancy for monitoring purposes, because each processor has the independent capability to shut down or limit the functionality of the medical equipment under error conditions. Standards and recommendations even exist for multiple-processor medical equipment which delineate the responsibilities of the monitoring processors.

SUMMARY OF THE INVENTION

The present invention has evolved from a desire to achieve a high degree of reliability for monitoring purposes in a multiple-processor electrosurgical generator that delivers electrosurgical energy for surgical procedures. A control processor generates a patterned pulse signal that defines a pattern of pulses that is used to generate output electrosurgical energy. A monitor processor receives the patterned pulse signal and a mode signal indicative of activation of a selected mode of operation of the electrosurgical generator. To determine whether the electrosurgical generator is functioning in the proper selected mode, the monitor processor counts the number of pulses in the patterned pulse signal and compares it to an expected number of pulses for the selected mode. If the counted number of pulses is the same as, or within an acceptable range of, the expected number of pulses, then the monitor processor determines that the electrosurgical generator is functioning in the selected mode. If the counted number of pulses is not the same as, or not within the acceptable range of, the expected number of pulses, then the monitor processor may take appropriate action, such as issuing an error indication to the surgeon and/or causing the electrosurgical generator to terminate delivery of the electrosurgical energy or to shut down.

In accordance with these improvements, the present invention involves a method of evaluating functionality of an electrosurgical generator. A patterned pulse signal is generated having a plurality of drive pulses. The patterned pulse signal is a signal with which the electrosurgical output power is generated. A number of the drive pulses in the patterned pulse signal is counted. The counted number of drive pulses is compared to an expected number of drive pulses. An error condition is indicated when the counted number of drive pulses and the expected number of drive pulses differ by a predetermined amount, which may preferably be one or more. Additionally, the electrosurgical output power is preferably controlled by adjusting a width of the drive pulses, for which a minimum width may be established. Furthermore, when the width of the drive pulses is about at the minimum width, the patterned pulse signal may preferably still be generated. Also, the method may preferably be combined with performing a power-related check on the electrosurgical output power, and indicating an error condition when a calculated power level is outside of a predetermined range.

Alternatively, the present invention involves a method of evaluating functionality of an electrosurgical generator which delivers electrosurgical output power under a plurality of modes of operation. One of the modes of operation under which the electrosurgical generator is to deliver the electrosurgical output power is indicated. The electrosurgical output power is generated by generating a patterned pulse signal in accordance with the indicated mode of operation. The patterned pulse signal is detected. It is determined from the patterned pulse signal whether the electrosurgical output power is being generated according to the indicated mode of operation. An error condition is then indicated when it is determined that the electrosurgical output power is not being generated according to the indicated mode of operation.

Additionally, the present invention involves an electrosurgical generator which delivers electrosurgical output power according to a selected mode signal. The electrosurgical generator includes a control processor and a monitor processor. The control processor generates a patterned pulse signal in accordance with the selected mode signal. The patterned pulse signal includes a series of drive pulses which contribute to generating the electrosurgical output power. The monitor processor is connected to the control processor and receives the patterned pulse signal, counts a number of the drive pulses in the patterned pulse signal, determines an expected number of drive pulses in accordance with the selected mode signal, compares the counted number of drive pulses with the expected number of drive pulses and indicates an error condition when the counted number of drive pulses and the expected number of drive pulses differ by a predetermined amount. The electrosurgical generator responds to the indication of the error condition by either issuing an error indication or terminating the delivery of output power.

A more complete appreciation of the present invention and its scope, and the manner in which it achieves the above noted and other improvements, can be obtained by reference to the following detailed description of presently preferred embodiments taken in connection with the accompanying drawings, which are briefly summarized below, and the appended claims.

DETAILED DESCRIPTION

Figure 1:
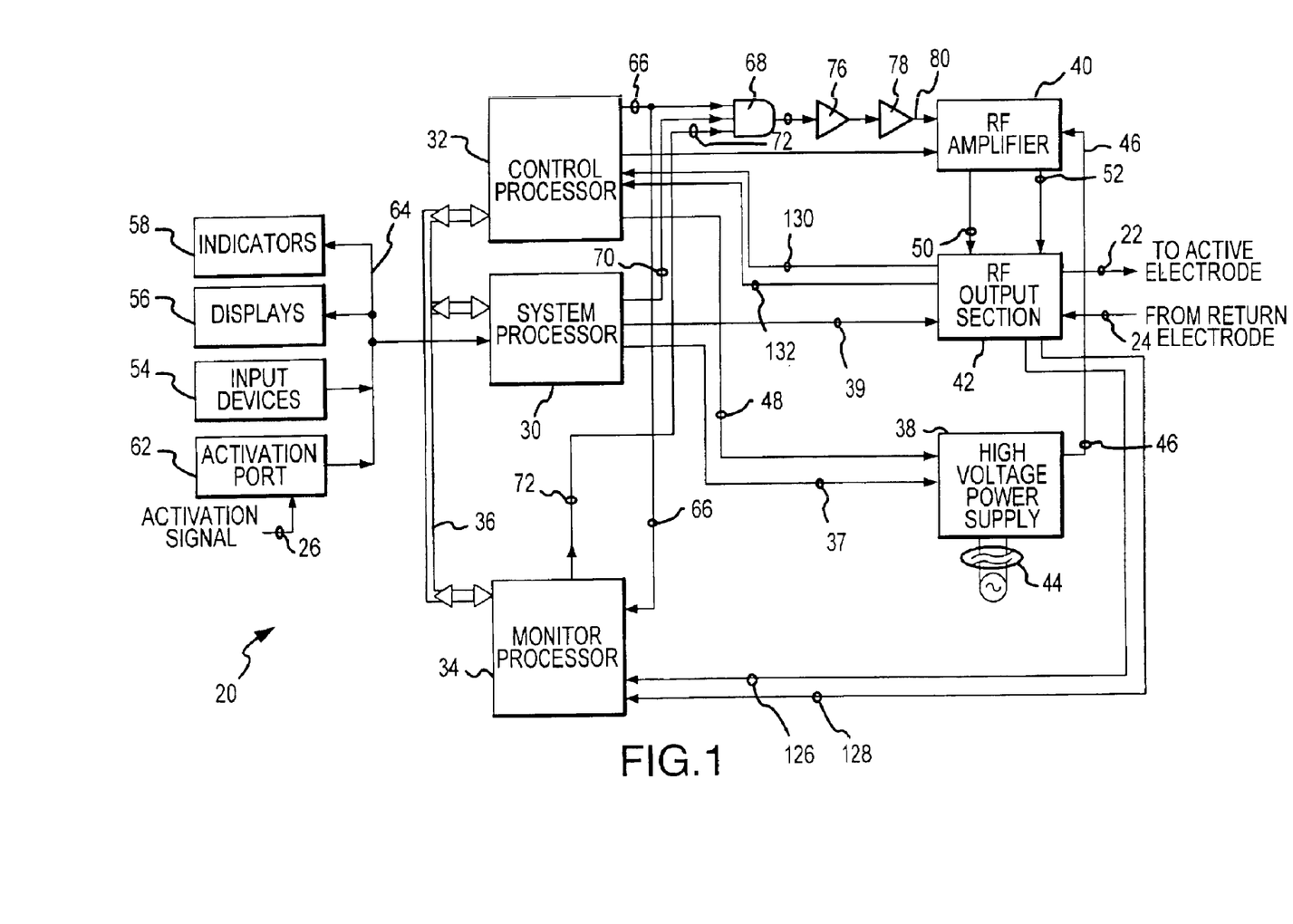
FIG. 1 is a block diagram of a multiple processor electrosurgical generator incorporating the present invention.

An electrosurgical generator 20, shown in FIG. 1, supplies electrosurgical output voltage and output current at 22, which is conducted to an active electrode (not shown) for monopolar and bipolar electrosurgery. Current is returned at 24 to the electrosurgical generator 20 from a return electrode (not shown), after having been conducted through the tissue of the patient. The generator 20 is activated to deliver the electrosurgical output power at 22 by activation signals supplied at 26. The activation signal at 26 is asserted upon closing a switch on a handpiece (not shown) which supports the active electrode and is held by the surgeon. The activation signal at 26 may also be asserted from a conventional foot pedal switch (not shown) which is depressed by foot pressure from the surgeon.

The electrosurgical generator 20 includes a system processor 30, a control processor 32, and a monitor processor 34. The system processor 30 generally controls the overall functionality of the electrosurgical generator 20. The system processor 30 includes nonvolatile memory (not shown) containing programmed instructions to be downloaded to the other processors 32 and 34 to establish the functionality of the control and monitor processors 32 and 34. The processors 30, 32 and 34 communicate with each other over a system bus 36. In general, the system processor 30 supervises and controls, at a high level, the entire electrosurgical generator 20. Thus, the system processor 30 supplies a power supply enable signal 37 to the high voltage power supply 38 to enable the high voltage power supply 38. The system processor 30 also supplies an output select signal at 39 to the RF output section 42. The output select signal at 39 causes the RF output section 42 to output the desired electrosurgical energy at 22 to the active electrode of a selected handpiece (not shown) connected to an output connector (not shown) for monopolar or bipolar electrosurgery.

The primary functionality of the control processor 32 is to establish and regulate the power delivered from the electrosurgical generator 20 at 22. The control processor is connected to a high voltage power supply 38, an RF amplifier 40, and an RF output section 42. The high voltage power supply 38 generates a DC operating voltage by rectifying conventional alternating current (AC) power supplied by conventional mains power lines 44, and delivers the DC operating voltage to the RF amplifier 40 at 46. The control processor 32 sets the voltage level for the DC operating voltage at 46 by a voltage-set signal at 48 supplied to the high voltage power supply 38. The RF amplifier 40 converts the DC operating voltage into monopolar drive signals 50 and bipolar drive signals 52 having an energy content and duty cycle appropriate for the amount of power and the mode of electrosurgical operation which have been selected by the surgeon. The RF output section 42 converts the monopolar and bipolar drive signals 50 and 52 into the RF voltage and current waveforms and supplies those waveforms to the active electrode at 22 as the output power from the electrosurgical generator 20.

The basic function of the monitor processor 34 is to monitor the functionality of the high voltage power supply 38 and the RF output section 42, as well as to monitor the functions of the control processor 32. If the monitor processor 34 detects a discrepancy in the output electrosurgical energy, or a discrepancy in the expected functionality of the control processor 32, a failure mode is indicated and the monitor processor 34 terminates the delivery of output electrosurgical energy from the electrosurgical generator 20.

The processors 30, 32 and 34 are conventional microprocessors, microcontrollers or digital signal processors, all of which are essentially general purpose computers that have been programmed to perform the specific functions of the electrosurgical generator 20.

The electrosurgical generator 20 also includes user input devices 54 which allow the user to select the mode of electrosurgical operation (cut, coagulation or a blend of both) and the desired amount of output power. In general, the input devices 54 are dials and switches that the user manipulates to supply control, mode and other information to the electrosurgical generator. The electrosurgical generator 20 also includes information output displays 56 and indicators 58. The displays 56 and indicators 58 provide feedback, menu options and performance information to the user. The input devices 54 and the output displays 56 and indicators 58 allow the user to set up and manage the operation of the electrosurgical generator 20.

The activation signals at 26 are applied from the finger and foot switches (not shown) to an activation port 62. The system processor 30 reads the activation signals at 26 from the port 62 to control the power delivery from the electrosurgical generator 20. The components 54, 56, 58 and 62 are connected to and communicate with the system processor 30 by a conventional input/output (I/O) peripheral bus 64, which is separate from the system bus 36.

To generate the electrosurgical energy at 22, the control processor 32 sets the voltage level of the DC operating voltage output at 46 from the high voltage power supply 38 by the voltage set signal at 48. The control processor 32 then generates a patterned pulse signal at 66 and sends it to an enable AND logic gate 68, where the patterned pulse signal at 66 is logically ANDed with enable signals 70 and 72 supplied by the system processor 30 and the monitor processor 34, respectively. The output of the enable logic gate 68 is supplied to a line driver 76 and a receiver 78 in series. The output of the line driver 76 and the receiver 78 forms a power driving signal at 80. The power driving signal at 80 is supplied to the RF amplifier 40. The RF amplifier 40 converts the DC operating voltage at 46 into the monopolar and bipolar drive signals at 50 and 52 according to the power driving signal at 80 formed from the patterned pulse signal at 66 output by the control processor 32. The output select signal at 39 from the system processor 30 then causes the RF output section 42 to output either the monopolar or bipolar drive signal at 50 or 52 as the electrosurgical energy at 22 to the selected handpiece (not shown).

The line driver 76 is preferably a conventional op amp. The line driver 76 and receiver 78 preferably isolate the high-voltage electronics of the RF amplifier 40 from the system, control and monitor processors 30, 32 and 34.

To shut down the electrosurgical generator 20 or to terminate the delivery of power from the electrosurgical generator 20, the monitor processor 34 deasserts the monitor enable signal 72 and/or the system processor 30 deasserts the amplifier enable signal 70. The assertion of both enable signals 70 and 72 to the enable logic gate 68 are required for the formation of the power driving signal at 80 from the patterned pulse signal at 66 through the enable logic gate 68, the line driver 76 and the receiver 78. Deasserting either one of the enable signals 70 or 72 prevents the enable logic gate 68 from conducting the patterned pulse signal at 66 through to the line driver 76 and the receiver 78 to form the power driving signal at 80 supplied to the RF amplifier 40. Without the assertion of the power driving signal at 80, the RF amplifier 40 will not deliver the monopolar or bipolar drive signals at 50 and 52 to the RF output section 42, and the electrosurgical generator 20 will not deliver output power or will terminate the delivery of output power.

Figure 3:
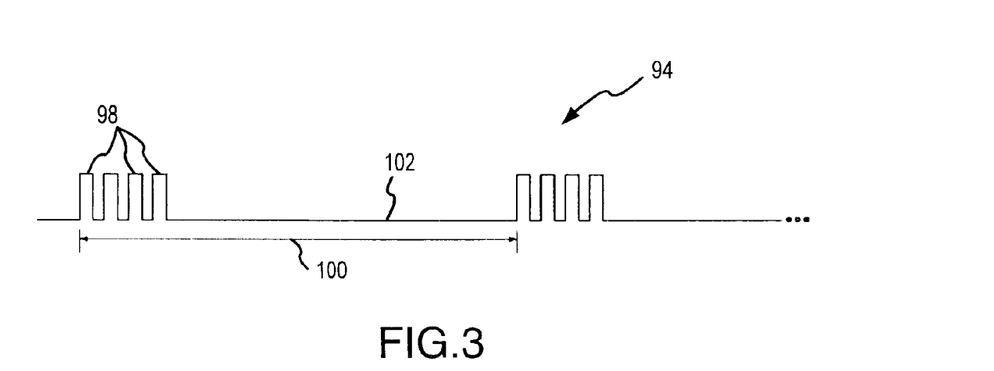
Figure 4:
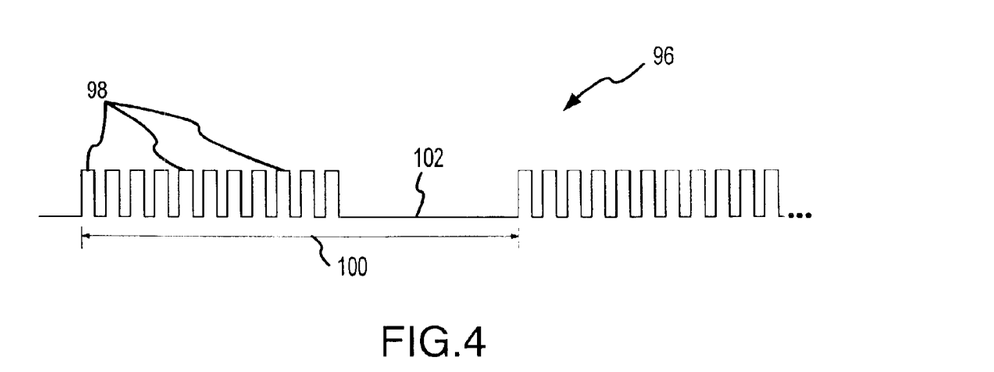

The patterned pulse signal at 66 is generally a waveform (e.g. 92, 94 and 96, shown in FIGS. 2, 3 and 4) formed of a patterned series of drive pulses 98 within a drive cycle 100 that repeats continuously during the selected mode of operation. The waveforms 92, 94 and 96 are examples for cut, coagulation and blend modes of operation, respectively. The pattern of the drive pulses 98, including the time width of each drive cycle 100, is fixed by the system processor 30 in accordance with the selected mode of operation. In most cases, the time width of each drive cycle 100 is approximately the same for the cut, coagulation and blend modes of operation, but the pattern of the drive pulses 98 within the drive cycles 100 are different, as shown in FIGS. 2–4.

Figure 2:
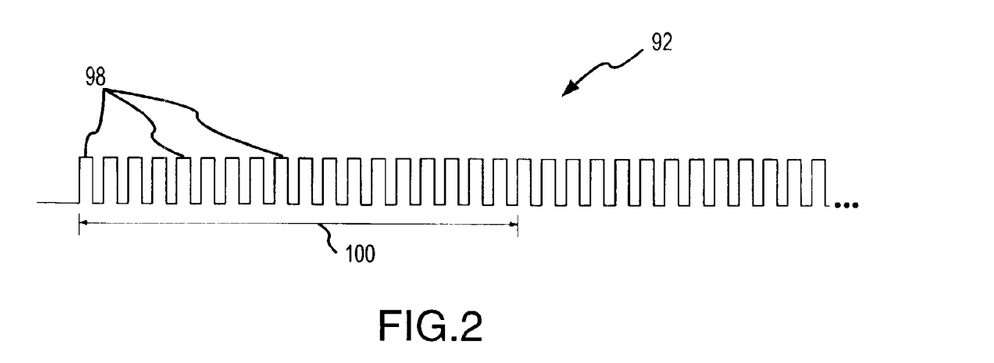
FIGS. 2, 3 and 4 are waveforms generated in the electrosurgical generator shown in FIG. 1.

A continuous uninterrupted sequence of the drive pulses 98 defines the cut pattern (waveform 92), as shown in FIG. 2. A repeating duty cycle application of the drive pulses 98 defines the coagulation pattern (waveform 94) and the blend pattern (waveform 96), as shown in FIGS. 3 and 4, respectively. In other words, no drive pulses 98 are delivered for an "off" time 102 during part of the drive cycle 100. Other specialized modes of operation exist as subsets of these three basic modes, and the amounts of coagulation in the coagulation mode and of cutting and coagulation in the blend mode is varied by adjusting the duty cycle of the drive cycle 100. Once the mode is selected, the pattern of drive pulses 98 defined by that selected mode remains unchanged until a different mode is selected. The width of the drive pulses 98, however, may be changed longer or shorter throughout the surgical procedure in order to regulate the output power.

The energy level of the output power at 22 (FIG. 1) is established by the width of the drive pulses 98 and the voltage of the high voltage power supply 38 (FIG. 1) for each drive cycle 100. The width of each drive pulse 98 is established by a number of equal-width steps dependent on the period of the clock (not shown) of the control processor 32 (FIG. 1). The number of equal-width steps is established by a pulse width count, which is initially set by the system processor 30 as representing the desired initial pulse width of the drive pulses 98. The amount of power transferred by the RF amplifier 40 (FIG. 1) in response to each drive pulse 98 is directly related to the width of each drive pulse 98.

Thus, the width of the drive pulses 98 is increased and decreased in order to regulate the power output during each electrosurgical procedure.

In order to monitor, or check, the mode of operation, as well as to achieve a high degree of reliability for monitoring purposes, the monitor processor 34 (FIG. 1) receives mode information, or a mode signal, from the system processor 30 (FIG. 1) through the system bus 36 (FIG. 1), and the patterned pulse signal at 66 (FIG. 1) from the control processor 32 (FIG. 1). The mode signal received by the monitor processor 34 includes information regarding the pattern of the drive pulses 98 (FIGS. 2–4) for the patterned pulse signal 66 generated by the control processor 32. Thus, the monitor processor 34 has information regarding the expected number of pulses that should be in the patterned pulse signal at 66 in a given amount of time. The monitor processor 34 counts the drive pulses 98 (e.g. typically on the rising edge of each drive pulse 98) in the patterned pulse signal at 66 in the given amount of time and compares the number of drive pulses 98 counted with the number of drive pulses 98 expected. If the difference between the counted and expected number of drive pulses 98 is within an acceptable limit, then it is confirmed that the electrosurgical generator 20 is functioning in the proper mode of operation. Otherwise, if the difference is greater than the acceptable limit, then an error or failure condition is indicated and the monitor processor 34 takes appropriate action, such as causing the electrosurgical generator 20 to issue an error indication, to stop producing the electrosurgical energy and/or to shut down.

The time period during which the monitor processor 34 (FIG. 1) counts the drive pulses 98 (FIGS. 2–4) is preferably longer than one drive cycle 100. Additionally, the counting time period is preferably long enough to minimize potential counting errors that may result due to the lack of clock synchronization between the control processor 32 (FIG. 1), which generates the drive pulses 98, and the monitor processor 34 (FIG. 1), which counts the drive pulses 98. An acceptable counting time period is about two to three of the drive cycles 100 or more.

The comparison of the counted and expected number of drive pulses 98 (FIGS. 2–4) allows the difference between the counted and expected number of drive pulses 98 to be within an acceptable limit, or range, since the monitor processor 34 (FIG. 1) may not be synchronized with the operation of the control processor 32 (FIG. 1), particularly since the control and monitor processors 32 and 34 may not operate at the same clock speed. Thus, some error between the counted and expected number of drive pulses 98 may be expected and taken into consideration.

Figure 5:
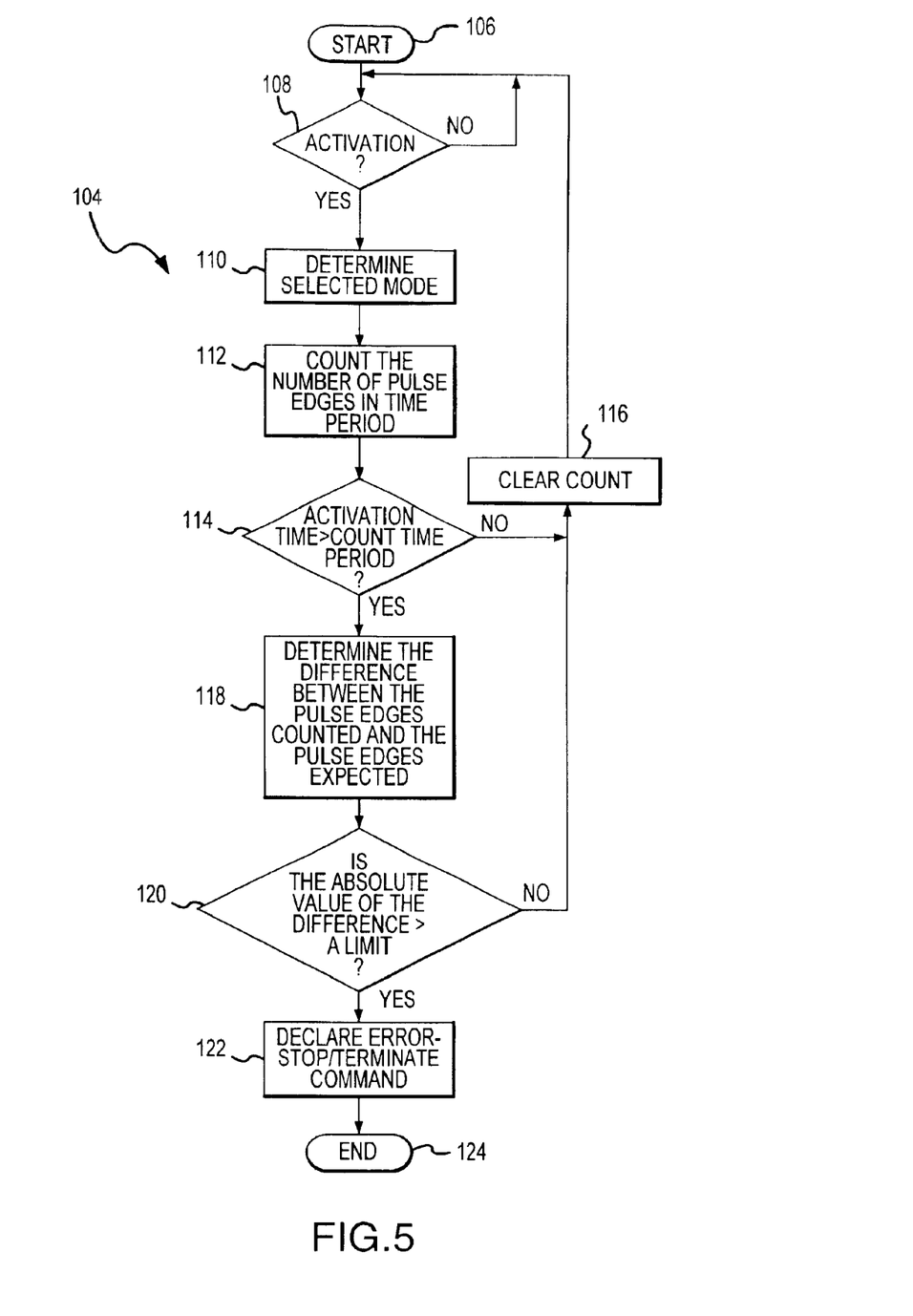
FIG. 5 is a flow chart for a procedure for verifying a mode of operation of the electrosurgical generator shown in FIG. 1.

A procedure 104 performed by the monitor processor 34 (FIG. 1) for checking the mode of operation is shown in FIG. 5. The mode checking procedure 104 starts at 106 and waits for activation of the electrosurgical generator at 108. Such activation is generally indicated to the monitor processor 34 by the system processor 30 (FIG. 1) in response to the activation signal at 26 being supplied to the system processor 30. The selected mode of operation is then determined at 110 according to the mode information provided from the system processor 30 to the monitor processor 34. Alternatively, the pattern or number of the drive pulses 98 (FIGS. 2, 3 and 4) is supplied to the monitor processor 34 in the mode information. The drive pulses 98, or pulse edges, are then counted in the counting time period at 112. Then it is determined at 114 whether the time length of the indicated activation is greater than the counting time period. If not, then it is assumed that the activation ended before the counting completed at 112, so the count is invalid and cannot be used to verify the mode of operation. Therefore, the count is cleared at 116, and the mode check procedure 104 returns to 108 to wait for the next activation. On the other hand, if the time length of the indicated activation is greater than the counting time period, as determined at 114, then the count is valid. In this case, the difference between the number of counted drive pulses 98 and the number of expected pulses is calculated at 118. The number of expected pulses depends on the selected mode determined at 110 or the pattern, or number, of pulses indicated in the mode information. It is then determined at 120 whether the absolute value of the difference calculated at 118 is greater than an acceptable limit. The acceptable limit is preferably determined empirically and depends on the selected mode. If the absolute value of the difference calculated is greater than the acceptable limit, as determined at 120, then an error is declared at 122 and the mode check procedure 104 ends at 124. On the other hand, if the absolute value of the difference calculated is not greater than the acceptable limit, as determined at 120, then the count is cleared at 116 and the mode check procedure 104 returns to 108 to wait for the next activation.

The control processor 32 (FIG. 1) is preferably programmed such that, to reduce the power output to almost zero, the width of the drive pulses 98 (FIGS. 2–4) of the patterned pulse signal at 66 (FIG. 1) is not decreased to zero, but to a minimum width. At the minimum width, attenuation properties of the line driver 76 and receiver 78 (FIG. 1) render them unable to pass the drive pulses 98 of the patterned pulse, signal applied at 66, when received through the enable AND logic gate 68 (FIG. 1). Thus, the minimum width of the drive pulses 98 results in the delivery of no power driving signal at 80, (FIG. 1), which results in no output power from the RF amplifier 40. In this case, since the drive pulses 98 of the patterned pulse signal 66 have not been reduced to zero, but remain at minimally narrow widths, the mode check can still be performed. In other words, the minimum width of the drive pulses 98 enables the mode check performed by the monitor 15, processor 34 (FIG. 1) to be able to determine that the electrosurgical generator 20 is operating in the proper mode, even when no power is being output.

Additionally, rather than basing the mode check on an acceptable limit for the difference between the counted and expected number of drive pulses 98 (FIGS. 2–4), as determined at 120 (FIG. 5) of the mode check procedure 104 (FIG. 5), the mode check could require the counted and expected number of drive pulses 98 to be identical. Alternatively, the acceptable limit for the difference may be based on a percentage of the expected number of drive pulses, wherein the percentage is empirically determined for each mode of operation.

The present invention is particularly advantageous in a situation where the monitor processor 34 (FIG. 1) also monitors the power output of the electrosurgical generator 20 (FIG. 1) using a power-related check. The first aforementioned patent application describes a power-related check, or monitoring function, incorporated in the electrosurgical generator 20. The monitor processor 34 receives current and voltage feedback signals 126 and 128 (FIG. 1) from the RF output section 42 (FIG. 1) indicating the current and voltage of the output electrosurgical energy, from which the power level can be calculated. The control processor 32 (FIG. 1) also receives current and voltage feedback signals 130 and 132 (FIG. 1) from the RF output section 42 separately indicating the current and voltage of the output electrosurgical energy, from which the power level can be separately calculated. The power-related check may, thus, ensure that the electrosurgical generator is functioning with the proper power output level given the desired mode of operation and/or that the control processor 32 and the monitor processor 34 have both calculated about the same power output level, as described in the first aforementioned application. However, there are situations in which the power-related checks may not produce a correct failure or non-failure indication. For example, the power-related checks have no data on which to base the checks if the power output is at or near zero, which can occur often in normal non-failure electrosurgical situations, as well as in failure conditions. As described above, however, the minimum pulse width enables the mode check to confirm whether the electrosurgical generator is at least functioning in the proper mode, so that a failure condition can be avoided when one is not actually indicated.

Additionally, given the large number and range of modes of operation in electrosurgery, and since there may be a considerable range of allowable power levels for each mode of operation, a proper power output for one mode may resemble a proper power output for a different mode. Thus, the power-related check may determine that the output power is proper for the intended mode of operation and that, no error has occurred, even when an error has, in fact, occurred that has caused the electrosurgical generator 20 to operate in the wrong mode. The mode check, though, would detect such a failure.

Thus, the mode check performed by the present invention can detect an error condition that power-related checks cannot detect and can avoid an error condition when power-related checks cannot be performed. The mode check may serve as a backup check for power-related checks.

On the other hand, the power-related check described in the first aforementioned application can detect errors that cannot be detected by the present invention. For instance, even if the mode check determines that electrosurgical generator 20 (FIG. 1) is delivering the electrosurgical energy in the selected mode of operation, it is still necessary to further determine whether the power level of the electrosurgical energy is within an acceptable range. Thus, the monitor processor 34 (FIG. 1) calculates the power output from the current and voltage feedback signals 126 and 128 (FIG. 1) from the RF output section 42 (FIG. 1) and determines whether the power output level is within the acceptable range, dependent on the mode of operation, as described in the first aforementioned application.

The present invention offers the improvement and advantage of being able to determine whether a failure condition has occurred in many situations where other checks cannot. The electrosurgical generator can be prevented from operating under conditions which might possibly cause a risk to the patient and can be assured of operating under conditions where the output power and performance of the electrosurgical generator is more reliably delivered. Many other benefits, advantages and improvements in monitoring the proper functionality of the electrosurgical generator will also be apparent upon gaining a full appreciation of the present invention.

Presently preferred embodiments of the invention have been described with a degree of particularity. This description has been made by way of preferred example. It should be understood that the scope of the invention is defined by the following claims, and should not be unnecessarily limited by the detailed description of the preferred embodiments set forth above.

What is claimed is:

1. A method of evaluating functionality of an electrosurgical generator which delivers electrosurgical output power from an output section of the electrosurgical generator in accordance with a selected mode of operation of the electrosurgical generator, comprising:

generating a patterned pulse signal formed by a plurality of drive pulses in accordance with the selected mode of operation;

applying the drive pulses of the patterned pulse signal to the output section of the electrosurgical generator;

converting energy represented by the drive pulses to electrosurgical output power;

within the output section of the electrosurgical generator;

counting the number of drive pulses in the patterned pulse signal applied to the output section;

establishing a predetermined expected number of drive pulses in accordance with the selected mode of operation;

comparing the counted number of drive pulses to the expected number of drive pulses; and indicating an error condition when the counted number of drive pulses and the expected number of drive pulses differ by a predetermined finite amount.

2. A method as defined in claim 1, further comprising:

controlling the electrosurgical output power by adjusting a width of the drive pulses without varying the number of drive pulses in the patterned pulse signal for the selected mode of operation.

3. A method as defined in claim 2, further comprising:

establishing a minimum width for each of the drive pulses at which the output section does not create electrosurgical output power despite application of the minimum-width drive pulses to the output section; and counting the number of minimum-width drive pulses and comparing the counted number of minimum-width drive pulses to the expected number of drive pulses and indicating the error condition, all without delivering output power.

4. A method as defined in claim 3, further comprising:

preventing the width of the drive pulses from reducing below a minimum width at which the drive pulses can be counted.

5. A method as defined in claim 4, further comprising:

performing an output power-related check on the electrosurgical output power by sensing output voltage and output current values of the delivered output power and calculating the output power based on the sensed output voltage and current values;

performing the output power-related check when generating the patterned pulse signal with minimum-width drive pulses; and evaluating the functionality of the electrosurgical generator in the selected mode of operation when no output power is delivered as a result of the minimum-width drive pulses.

6. A method as defined in claim 5, further comprising:

performing the power-related check when the drive pulses of the patterned pulse signal have a width greater than the minimum width and are sufficient to cause the output section to create output power having the output voltage and current values; and indicating an error condition when the output power level calculated from the output voltage and current is outside of a predetermined range established by the selected mode of operation and the width of the drive pulses of the patterned pulse signal.

7. A method as defined in claim 1, further comprising:
indicating the error condition when the counted number of drive pulses and the expected number of drive pulses differ by at least one.

8. A method as defined in claim 1, further comprising:
indicating the error condition when the counted number of drive pulses and the expected number of drive pulses differ by a predetermined percentage of the expected number of drive pulses.

9. A method as defined in claim 1, wherein the electrosurgical generator includes a control processor which controls the delivery of the electrosurgical output power and also includes a monitor processor which monitors performance of the electrosurgical generator, and further comprising:
generating the patterned pulse signal of drive pulses using the control processor; and
counting the number of drive pulses using the monitor processor.

10. A method as defined in claim 1, further comprising:
generating the patterned pulse signal during a pattern time period;
repeating the patterned pulse signal during successive pattern time periods; and
counting the number of the drive pulses over a counting time period that is greater than at least one of the pattern time periods.

11. A method as defined in claim 10, further comprising:
counting the number of the drive pulses over a counting time period which is equal to at least two of the successive pattern time periods.

12. A method as defined in claim 1, further comprising:
generating the patterned pulse signal with the drive pulses arranged in a pattern that repeats over successive time periods and with an off time during which no pulses occur;
counting the number of the drive pulses in the patterned pulse signal over a counting time period that is sufficiently long to ensure that all of the drive pulses in at least one of the successive time periods are within the counting time period.

13. A method of evaluating functionality of an electrosurgical generator which delivers electrosurgical output power, comprising:
generating a patterned pulse signal with which the electrosurgical output power is generated, the patterned pulse signal having a plurality of drive pulses that are arranged in a pattern that repeats over successive time periods and that includes an off time off time during which no pulses occur;
counting a number of the drive pulses in the patterned pulse signal over a counting time period that is sufficiently long to ensure that all of the drive pulses in at least one of the successive time periods are within the counting time period;
comparing the counted number of drive pulses to an expected number of drive pulses; and
indicating an error condition when the counted number of drive pulses and the expected number of drive pulses differ by a predetermined amount.

14. A method as defined in claim 13, further comprising:
controlling the electrosurgical output power by adjusting a width of the drive pulses.

15. A method as defined in claim 14, further comprising:
establishing a minimum width for the drive pulses.

16. A method as defined in claim 13, wherein the electrosurgical output power is dependent on a width of the drive pulses, and further comprising:
preventing the width of the drive pulses from reducing below a minimum width.

17. A method as defined in claim 16, wherein the electrosurgical generator performs a power-related check on the electrosurgical output power, and further comprising:
generating the patterned pulse signal having the drive pulses when the width of the drive pulses is at the minimum width.

18. A method as defined in claim 13, further comprising:
indicating the error condition when the counted number of drive pulses and the expected number of drive pulses differ by at least one.

19. A method as defined in claim 13, further comprising:
indicating the error condition when the counted number of drive pulses and the expected number of drive pulses differ by a predetermined percentage of the expected number of drive pulses.

20. A method as defined in claim 13, further comprising:
performing a power-related check on the electrosurgical output power, including calculating a power level of the electrosurgical output power; and
indicating an error condition when the calculated power level is outside of a predetermined range.

21. A method as defined in claim 13, wherein the electrosurgical generator includes a control processor which controls the delivery of the electrosurgical output power and also includes a monitor processor which monitors performance of the electrosurgical generator, and further comprising:
generating the patterned pulse signal using the control processor; and
counting the number of drive pulses using the monitor processor.

22. A method as defined in claim 13, wherein the drive pulses in the patterned pulse signal are arranged in a pattern that repeats over successive time periods, and further comprising:
counting the number of the drive pulses in the patterned pulse signal over a counting time period that is greater than at least one of the successive time periods.

23. A method as defined in claim 22, further comprising:
counting the number of the drive pulses in the patterned pulse signal over at least two of the successive time periods.

24. A method as defined in claim 13, wherein the electrosurgical
generator delivers the electrosurgical output power from an output section in accordance with a selected mode of operation of the electrosurgical generator, and further comprising:
generating the patterned pulse signal in accordance with the selected mode of operation;
applying the drive pulses of the patterned pulse signal to the output section of the electrosurgical generator;
converting energy represented by the drive pulses to electrosurgical output power within the output section of the electrosurgical generator;
counting the number of drive pulses in the patterned pulse signal applied to the output section;

establishing the expected number of drive pulses in accordance with the selected mode of operation; and indicating the error condition when the counted number of drive pulses and the expected number of drive pulses differ by a predetermined finite amount.

25. A method of evaluating functionality of an electrosurgical generator which delivers electrosurgical output power under a plurality of modes of operation, comprising:

selecting one of the plurality of modes of operation for the electrosurgical generator to deliver the output power;

generating a patterned pulse signal in accordance with the selected mode of operation, the patterned pulse signal having a plurality of drive pulses and an off time during which no pulses occur arranged in a pattern that repeats over successive pattern time periods;

generating electrosurgical output power by using the patterned pulse signal;

detecting the drive pulses of the patterned pulse signal over at least one of the successive pattern time periods;

determining from the detected drive pulses whether the electrosurgical output power is being generated according to the selected mode of operation; and indicating an error condition upon determining that the electrosurgical output power is not being generated according to the selected mode of operation.

26. A method as defined in claim 25, further comprising:

controlling the amount of electrosurgical output power generated by adjusting a width of the drive pulses without varying the number of drive pulses in the patterned pulse signal for the selected mode of operation;

establishing a minimum width for each of the drive pulses which is insufficient to generate the output power despite the use of the patterned pulse signal;

reducing the generated output power to zero by reducing the width of the drive pulses to the minimum width;

detecting the minimum-width drive pulses of the patterned pulse signal;

determining from the detected minimum-width drive pulses whether the output power would be generated according to the selected mode of operation if the width of the drive pulses was increased from the minimum width; and indicating the error condition upon determining that the detected the minimum-width drive pulses are not in accordance with the selected mode of operation, while the generated output power is reduced to zero.

27. A method as defined in claim 26, wherein the electrosurgical generator includes a control processor which controls the delivery of the electrosurgical output power and also includes a monitor processor which monitors performance of the electrosurgical generator, and further comprising:

using the control processor to generate the patterned pulse signal of drive pulses; and using the monitor processor to detect the drive pulses of the patterned pulse signal and to determine from the detected drive pulses whether the electrosurgical output power would be generated according to the selected mode of operation.

28. A method as defined in claim 25, further comprising:

delivering the generated output power from the electrosurgical generator;

sensing characteristics of the output power delivered;

calculating a power level of the delivered electrosurgical output power from the sensed characteristics; and indicating an error condition when the calculated power level is outside of a predetermined range established by the selected mode of operation.

29. A method as defined in claim 28, further comprising:

calculating the power level of the delivered output power without reference to the patterned pulse signal.

30. A method as defined in claim 29, further comprising:

sensing output voltage and output current of the output power as the sensed characteristics used to calculate the power level.

31. A method as defined in claim 25, wherein the electrosurgical generator delivers the electrosurgical output power from an output section, and further comprising:

applying the drive pulses of the patterned pulse signal to the output section of the electrosurgical generator;

converting energy represented by the drive pulses to the output power within the output section of the electrosurgical generator; and detecting the drive pulses in the patterned pulse signal applied to the output section.

32. A method as defined in claim 31, further comprising:

establishing an expected number of drive pulses during each pattern time period in accordance with the selected mode of operation; and indicating the error condition when the counted number of drive pulses and the expected number of drive pulses differ by a predetermined finite amount.

33. A method as defined in claim 32, further comprising:

indicating the error condition when the counted number of drive pulses and the expected number of drive pulses differ by at least one.

34. A method as defined in claim 32, further comprising:

indicating the error condition when the counted number of drive pulses and the expected number of drive pulses differ by a predetermined percentage of the expected number of drive pulses.

35. A method as defined in claim 32, further comprising:

counting the number of the drive pulses over a counting time period that is greater than at least one of the pattern time periods.

36. A method as defined in claim 32, further comprising:

counting the number of the drive pulses over a counting time period which is equal to at least two of the successive pattern time periods.

37. A method as defined in claim 25, wherein the electrosurgical generator includes a control processor which controls the delivery of the electrosurgical output power and also includes a monitor processor which monitors performance of the electrosurgical generator, and further comprising:

using the control processor to generate the patterned pulse signal of drive pulses; and using the monitor processor to detect the drive pulses of the patterned pulse signal and to determine from the detected drive pulses whether the electrosurgical output power is being generated according to the selected mode of operation.

38. An electrosurgical generator which delivers electrosurgical output power according to a selected one of a plurality of different modes of operation, each mode represented by a different selected mode signal, comprising:

a control processor which generates a patterned pulse signal in accordance with the selected mode signal, the patterned pulse signal having a plurality of drive pulses and an off time during which no pulses occur arranged in a pattern that repeats over successive pattern time periods in at least one of the different modes of operation;

an output section receptive of the patterned pulse signal and operative to convert energy represented by the drive pulses into the delivered output power, the control processor applying the patterned pulse signal to the output section;

a monitor processor receptive of the patterned pulse signal and the selected mode signal, the monitor processor detecting the drive pulses of the patterned pulse signal over at least one of the successive pattern time periods, the monitor processor determining from the detected drive pulses whether the patterned pulse signal applied by the control processor to the output section is consistent with the selected mode signal, the monitor processor indicating an error condition upon determining that the patterned pulse signal applied by the control processor to the output section is inconsistent with the selected mode signal; and one of the control or monitor processors responding to the indication of the error condition by one of either issuing an alarm or terminating the delivery of the output power.

39. An electrosurgical generator as defined in claim 38 further comprising:

a system processor connected to the control processor and the monitor processor and which operatively oversees functionality of the control and monitor processors, the system processor generating the selected mode signal and sending the selected mode signal to the control processor and the monitor processor.

40. An electrosurgical generator as defined in claim 38, wherein:

the monitor processor counts the number of the drive pulses in the patterned pulse signal over the at least one pattern time period, determines from the selected mode signal an expected number of drive pulses which should occur over the at least one pattern time period, compares the counted number of drive pulses with the expected number of drive pulses, and indicates the error condition when the counted number of drive pulses and the expected number of drive pulses differ by a predetermined finite amount.

41. An electrosurgical generator as defined in claim 40, wherein:

the predetermined finite amount is at least one drive pulse.

42. An electrosurgical generator as defined in claim 40, wherein:

the predetermined finite amount is a predetermined percentage of the expected number of drive pulses.

43. An electrosurgical generator as defined in claim 40, wherein:

the monitor processor detects the drive pulses of the patterned pulse signal over a counting time period which is greater than one of the successive pattern time periods.

44. An electrosurgical generator as defined in claim 40, wherein:

the monitor processor detects the drive pulses of the patterned pulse signal over at least two successive pattern time periods.

45. An electrosurgical generator as defined in claim 38, wherein:

the control processor controls the amount of electrosurgical output power delivered by adjusting a width of the drive pulses without varying the number of drive pulses in the patterned pulse signal for each selected mode signal.

46. An electrosurgical generator as defined in claim 45, wherein:

the control processor establishes a minimum width for each of the drive pulses at which the output section does not create electrosurgical output power despite application of the minimum-width drive pulses to the output section; and the monitor processor counts the number of minimum-width drive pulses and compares the counted number with the expected number and indicates the error condition, when the output section does not deliver output power as a result of the application of the minimum-width drive pulses to the output section.

47. An electrosurgical generator as defined in claim 46, wherein:

the control processor prevents reducing the width of the drive pulses to a width less than the minimum width which the monitor processor can detect.

48. An electrosurgical generator as defined in claim 46, wherein:

the monitor processor senses values of output voltage and output current of the delivered output power and calculates the amount of output power delivered based on the sensed output voltage and output current values; and the monitor processor indicates an error condition when the output power level calculated from the sensed output voltage and current is outside of a predetermined range established by the selected mode signal.

49. An electrosurgical generator as defined in claim 48, wherein:

the monitor processor senses the values of the output voltage and the output current when the minimum-width drive pulses are applied to the output section.

* * * * *

UNITED STATES PATENT AND TRADEMARK OFFICE
CERTIFICATE OF CORRECTION

PATENT NO.        : 6,875,210 B2
APPLICATION NO.   : 10/299952
DATED             : April 5, 2005
INVENTOR(S)       : Tim Refior and Jim Pantera It is certified that error appears in the above-identified patent and that said Letters Patent is hereby corrected as shown below:

Column 10, claim 1, delete lines 13-15 and replace those lines with the following:

converting energy represented by the drive pulses to electrosurgical output power within the output section of the electrosurgical generator;

Signed and Sealed this
Twenty-second Day of February, 2011

David J. Kappos
*Director of the United States Patent and Trademark Office*